(12) United States Patent
Stahl et al.

(10) Patent No.: US 8,594,276 B2
(45) Date of Patent: Nov. 26, 2013

(54) SYSTEM AND METHOD FOR DYNAMIC STROBE ARC THERAPY

(75) Inventors: Johannes N. Stahl, Walnut Creek, CA (US); Himanshu P. Shukla, Lafayette, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 245 days.

(21) Appl. No.: 12/946,728

(22) Filed: Nov. 15, 2010

(65) Prior Publication Data

US 2011/0293067 A1 Dec. 1, 2011

(30) Foreign Application Priority Data

Jun. 1, 2010 (EP) ..................................... 10164658

(51) Int. Cl.
*A61N 5/10* (2006.01)
(52) U.S. Cl.
USPC .......................................................... 378/65
(58) Field of Classification Search
USPC ..................... 378/62, 65, 197, 196
See application file for complete search history.

(56) References Cited

U.S. PATENT DOCUMENTS

| | | | |
|---|---|---|---|
| 5,339,347 A | 8/1994 | Slatkin et al. | |
| 7,027,557 B2 | 4/2006 | Llacer | |
| 7,693,257 B2 | 4/2010 | Allison | |
| 2004/0071261 A1 | 4/2004 | Earl et al. | |
| 2006/0045238 A1 | 3/2006 | Nguyen | |
| 2007/0071168 A1* | 3/2007 | Allison et al. | 378/65 |
| 2008/0242969 A1 | 10/2008 | Sayeh et al. | |
| 2008/0298550 A1 | 12/2008 | Otto | |
| 2009/0180589 A1* | 7/2009 | Wang et al. | 378/65 |
| 2009/0225942 A1 | 9/2009 | Shepard et al. | |
| 2010/0104068 A1* | 4/2010 | Kilby et al. | 378/65 |
| 2010/0183120 A1 | 7/2010 | Nord et al. | |

* cited by examiner

*Primary Examiner* — Irakli Kiknadze

(57) ABSTRACT

Aspects may include movement of at least one device along a path to change an orientation of a target volume with respect to a radiation beam emitter, determination that the at least one device has reached a start position of a first path section associated with a first radiation treatment beam, emission, while the at least one device moves along the first path section, of the first radiation treatment beam from the radiation beam emitter toward a target volume, determination that the at least one device has reached a stop position of the first path section, ceasing emission of the first radiation treatment from the radiation beam emitter in response to the determination that the at least one device has reached a stop position of the first path section, determination that the at least one device has reached a start position of a second path section associated with a second radiation treatment beam, the start position of the second path section being different from the stop position of the first path section, and emission, while the at least one device moves along the second path section, of the second radiation treatment beam from the radiation beam emitter toward the target volume.

29 Claims, 6 Drawing Sheets

100

SYSTEM AND METHOD FOR DYNAMIC STROBE ARC THERAPY

CROSS-REFERENCE TO RELATED APPLICATIONS

The present application claims priority to U.S. Provisional Patent Application Ser. No. 61/219,662, filed on Jun. 23, 2009 and entitled "HYBRID ARC IMRT", the contents of which are incorporated herein by reference for all purposes.

The present application is a Continuation-in-Part of U.S. patent application Ser. No. 12/543,437, filed on Aug. 18, 2009 and entitled "SYSTEM AND METHOD FOR DYNAMIC STROBE ARC THERAPY", the contents of which are incorporated herein by reference for all purposes.

The present application claims priority to European Patent Application No. 10164658.6, filed on Jun. 1, 2010, the contents of which are incorporated herein by reference for all purposes.

BACKGROUND

1. Field

The embodiments described below relate generally to the delivery of radiation therapy to a patient according to a "dynamic strobe" delivery scheme. In some embodiments, the "dynamic strobe" delivery scheme may encompass and/or seamlessly combine with one or more other radiation therapy delivery methods.

2. Description

According to conventional radiation therapy, a beam of radiation is directed toward a tumor located within a patient. The radiation beam delivers a predetermined dose of therapeutic radiation to the tumor according to a treatment plan. The delivered radiation kills cells of the tumor by causing ionizations within the cells. A major concern is limiting the damage to healthy tissue surrounding the tumor.

FIG. 1 illustrates a conventional patient treatment process that includes radiation therapy. According to some examples of process 100, image data of a patient is acquired, and a target volume and critical internal structures are identified based on the image data during diagnosis (105). A radiation dose is prescribed (110) for achieving desired results with respect to the target volume while minimizing damage to the critical structures. Next, a treatment plan for delivering the dose is determined (115).

The treatment plan is then delivered (125) to the patient during several sessions, or "fractions", spaced over some period of days. Prior to each fraction, the patient is positioned (120) as required by the treatment plan. Such positioning may involve the use of lasers, skin markers, etc.

Various methods or modes of radiation therapy delivery have been proposed and utilized. A radiation therapy delivery system typically includes hardware and a control system optimized for one specific mode of radiation therapy delivery. Some modes of radiation therapy delivery include, for example, conventional IMRT, Dynamic Modulated Arc Therapy, CT-Guided IMRT (Intensity Modulated Radiation Therapy), and Volumetric Modulated Arc Therapy.

In a conventional IMRT system, beams with modulated intensity are generated at a number of fixed positions or angles around the patient. These beams are then delivered with the gantry stationary at each fixed position. The beam intensity is modulated by either superimposing several shapes at a fixed position ("Step and Shoot IMRT") or by moving leaves of a multileaf collimator ("MLC") across the beam with varying speeds ("Sliding Window IMRT"). In a Dynamic Modulated Arc therapy system the gantry of the delivery system performs a contiguous rotational motion (360 degrees or less per arc). Throughout the rotational motion, the beam remains on at constant dose rate, and the MLC leaves constantly re-form to maintain a shape which is conformal with the shape of the tumor, as viewed from the respective angle. The throughput of Dynamic Modulated Arc therapy is greater than in conventional IMRT, but requires more sophisticated control of the MLC leaves.

In a CT-Guided IMRT system, such as a TomoTherapy® system provided TomoTherapy Incorporated, a linear accelerator is mounted in a ring-shaped gantry and moves in a 360 degree rotation around the patient. The beam is always on during this motion and is partially blocked or unblocked by rapidly opening and closing the MLC leaves as the gantry rotates. In a Volumetric Modulated Arc Therapy system, such as provided by the RapidArc™ radiotherapy technology from Varian Medical Systems, an L-shaped gantry performs a 360 degree rotation around the patient. The beam is constantly on and the dose rate may be modulated. Also, the MLC leaves are in constant motion, thus creating different shapes as the gantry rotates. These latter two systems require complex and expensive components for synchronizing and controlling motion of the gantry and the MLC leaves.

During the treatment planning stage (115), a decision is made regarding which delivery mode to use. The decision may be based on a number of factors, including for example the patient's diagnosis, delivery system constraints, time issues related to schedules and availability of the patient and/or radiation therapy systems, etc. After the specific mode of delivery is decided, a treatment plan that is adapted to the delivery mode is determined.

Selection of a delivery mode involves trade-offs or compromises as described above. Other radiation therapy delivery modes which may be particularly suitable to certain applications are desired.

SUMMARY

To address at least the foregoing, some embodiments provide a system, method, apparatus, and means to move at least one device along a path to change an orientation of a target volume with respect to a radiation beam emitter, determine that the at least one device has reached a start position of a first path section associated with a first radiation treatment beam, emit, while the at least one device moves along the first path section, the first radiation treatment beam from the radiation beam emitter toward a target volume, determine that the at least one device has reached a stop position of the first path section, cease emission of the first radiation treatment from the radiation beam emitter in response to the determination that that the at least one device has reached a stop position of the first path section, determine that the at least one device has reached a start position of a second path section associated with a second radiation treatment beam, the start position of the second path section being different from the stop position of the first path section, and emit, while the at least one device moves along the second path section, the second radiation treatment beam from the radiation beam emitter toward the target volume Embodiments are not limited to those described herein, as those in the art can readily adapt the descriptions to create other embodiments and applications.

BRIEF DESCRIPTION OF THE DRAWINGS

The construction and usage of embodiments will become readily apparent from consideration of the following specification as illustrated in the accompanying drawings, in which like reference numerals designate like parts, and wherein.

DETAILED DESCRIPTION

Figure 1:
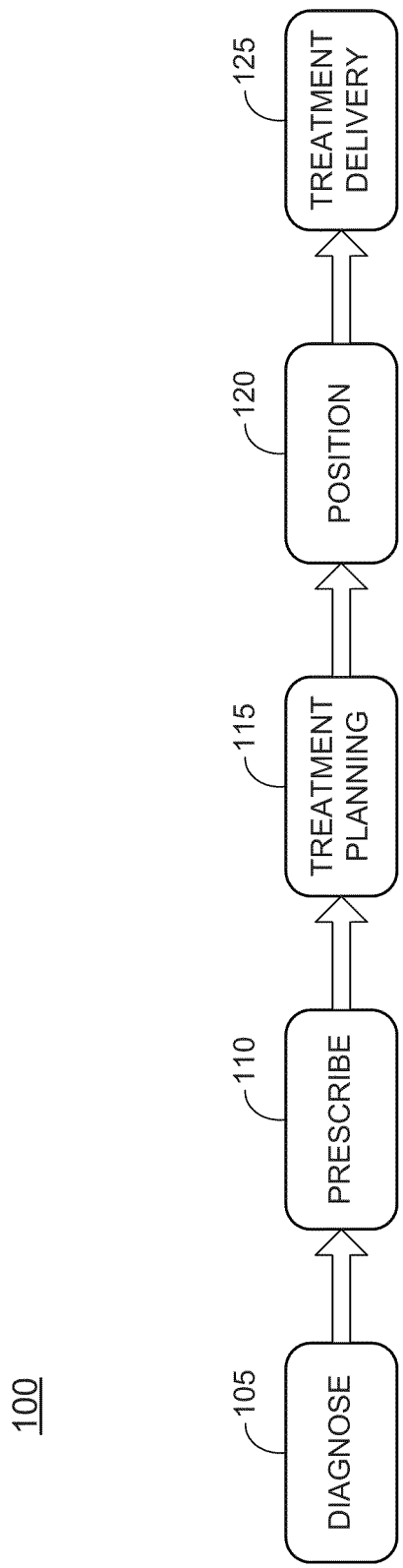
FIG. 1 is a diagram of a radiation therapy process, in accordance with some embodiments herein.

The following description is provided to enable any person in the art to make and use the embodiments described herein and sets forth the best mode contemplated therefor. Various modifications, however, will remain readily apparent to those in the art.

As a brief introduction to the features of some embodiments, a radiation treatment plan may define a path along which at least one device may be moved to change an orientation of a target volume with respect to a radiation emitting device, and a plurality of sections of the path. The device may include the radiation emitting device itself (e.g., where the path is at least a portion of the arc through which the radiation emitting device rotates via rotation of a gantry), and/or a treatment table on which a patient (within whom resides the target volume) is disposed. In the case of the treatment table, the path may include any positions through which the table may travel. Each path section may be associated with a respective radiation treatment beam. Also, each path section is associated with a start position and a stop position.

The treatment plan may be executed to move the at least one device along the path until a start position of a first path section is reached. The radiation beam emitter emits a radiation treatment beam associated with the first path section while the at least one device continues to move along the first path section. The radiation beam emitter ceases emission of the radiation treatment beam once the at least one device reaches the stop position of the first path section.

The at least one device continues to move along the path until reaching a start position of a next path section. The radiation beam emitter emits a radiation treatment beam associated with the next path section while the at least one device continues to move along the next path section. The radiation beam emitter ceases emission of the radiation treatment beam once the stop position of the next path section is reached.

The above operation may continue with respect to additional path sections. A gap may exist between two successive path sections, such that the stop position of path section differs from the start position of the successive path section. Accordingly, a radiation treatment beam is not emitted during motion of the at least one device between the two successive path sections.

The radiation treatment beam associated with the next path section may differ from the radiation treatment beam associated with the first path section in dose rate, cross-section (determined by MLC collimator leaves), and/or any other characteristic. These characteristics may be changed during movement of the at least one device from the stop position of the first path section to the start position of the next path section.

In some aspects, a path section is associated with more than one radiation treatment beam. A start position of a path section may coincide with a stop position of the path section, such that the at least one device pauses at the start/stop position for emission of a radiation treatment beam associated with the path section.

Figure 2:
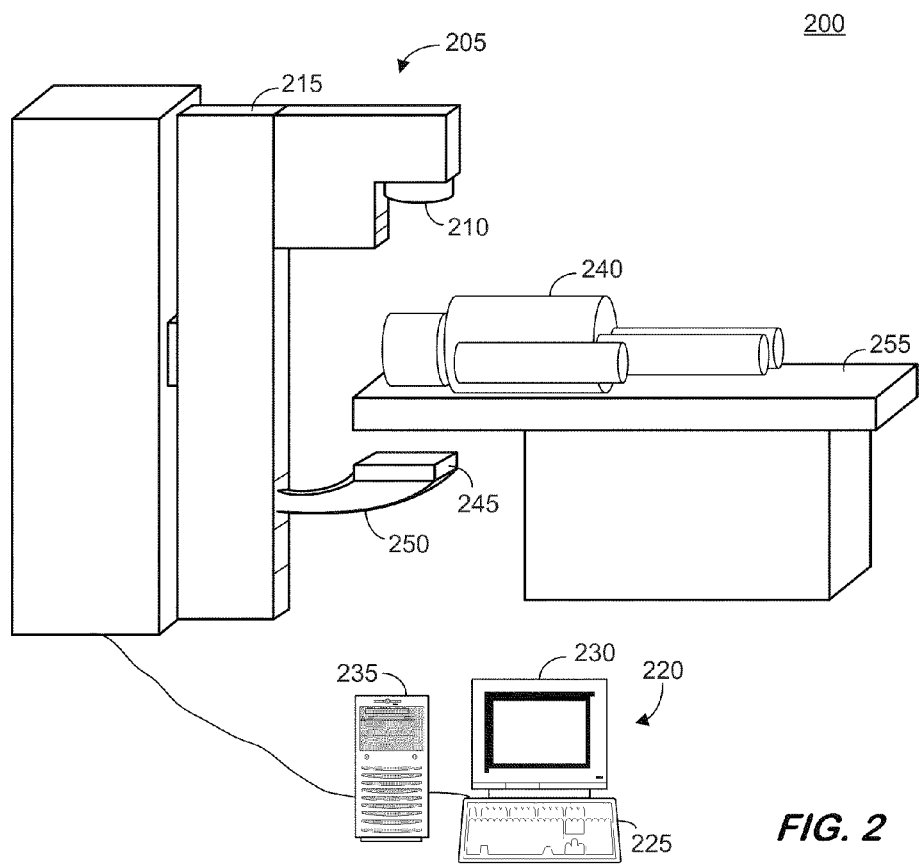
FIG. 2 is a perspective view of a radiation therapy system, according to some embodiments.

Some embodiments will be generally described in conjunction with system 200, a perspective view of which is provided in FIG. 2. Of course, systems other than system 200 of FIG. 2 may be used to implement embodiments described herein.

System 200 includes linear accelerator 205, operator console 220, patient 240, imaging device 245, and table 255. System 200 may be used to generate radiation for imaging and/or for radiation therapy. In this regard, patient 240 is positioned to receive a radiation dose according to a radiation treatment plan.

Linear accelerator 205 may deliver a radiation beam from treatment head 210 toward a volume of patient 240 that is located at an isocenter of accelerator 205. According to some embodiments, the radiation beam may comprise photon or electron radiation having energies in the megavoltage range. Treatment head 210 includes a beam-emitting device for emitting a radiation beam and a beam-shielding device or collimator for shaping the beam and for shielding sensitive surfaces from the beam. Treatment head 210 may also include an accessory tray to receive and securely hold attachments used during the course of treatment planning and treatment (such as, for example, reticles, wedges, or the like).

Imaging device 245 may comprise any system to acquire two-dimensional images based on photon radiation (i.e., X-rays) and/or electron radiation received from treatment head 210. Accordingly, imaging device 245 may be suitable for acquiring image data based on megavoltage radiation. Imaging device 245 may be used to acquire images for diagnosis, for verification and recordation of a patient position, for verification and recordation of internal structure positions, and/or for other purposes. In some instances, cone-beam reconstruction techniques may be used to construct three-dimensional images from two-dimensional images acquired by imaging device 245.

In some embodiments, imaging device 245 may be a flat-panel imaging device using a scintillator layer and solid-state amorphous silicon photodiodes deployed in a two-dimensional array. In other embodiments, imaging device 245 converts X-rays to electrical charge without requiring a scintillator layer. In such imaging devices, X-rays are absorbed directly by an array of amorphous selenium photoconductors. The photoconductors convert the X-rays directly to stored electrical charge that comprises an acquired image of a radiation field. Imaging device 245 may also comprise a CCD or tube-based camera. Such an imaging device may include a light-proof housing within which are disposed a scintillator, a mirror, and a camera.

Gantry 215 is rotatable around an axis before, during and after emission of the radiation beam. Rotation of gantry 215 may cause treatment head 210 and imaging device 245 to rotate around the isocenter such that the isocenter remains located between treatment head 210 and imaging device 245 during the rotation, while changing an orientation of a target volume at the isocenter with respect to treatment head 210.

Imaging device 245 may be attached to gantry 215 in any manner, including via extendible and retractable housing 250.

Table 255 supports patient 240 during radiation therapy. Table 255 may be movable, alone or in conjunction with gantry 215, to change an orientation of a target volume with respect to treatment head 210. Table 255 may be moved along any number or combination of axes.

Operator console 220 includes input device 225 for receiving instructions from an operator and output device 230, which may be a monitor for presenting operational parameters of linear accelerator 205 and/or interfaces for receiving instructions. Such instructions may include a selection from among a plurality of available radiation therapy processes. Output device 230 may also present images acquired by imaging device 245 to verify patient positioning prior to treatment delivery. Input device 225 and output device 230 are coupled to processor 235.

Processor 235 executes program code according to some embodiments. The program code may be executable to control system 200 to operate as described herein. The program code may be stored in any computer-readable medium, including but not limited to a fixed disk, an optical disk, flash memory, a CD-ROM, a DVD-ROM, a disk, a magnetic tape, and any other storage medium now known or that becomes known.

Operator console 220 may be located apart from linear accelerator 205, such as in a different room, in order to protect its operator from radiation. For example, accelerator 205 may be located in a heavily shielded room, such as a concrete vault, which shields the operator from radiation generated by accelerator 205.

FIG. 2 may include less or more elements than those shown. In addition, embodiments are not limited to the system and devices shown in FIG. 2.

Figure 3:
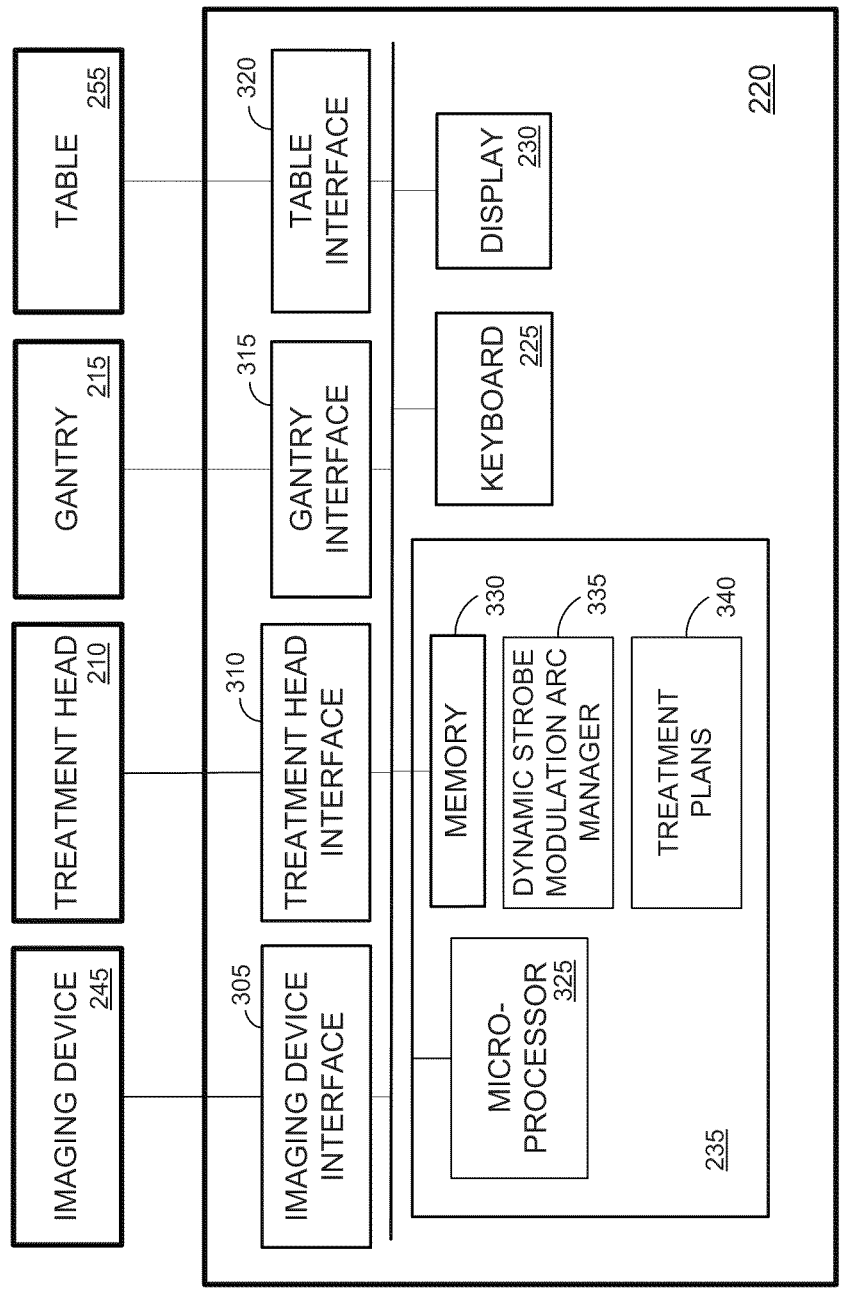
FIG. 3 is a block diagram of a radiation therapy system, according to some embodiments.

FIG. 3 is a block diagram of elements of system 200 according to some embodiments. As shown, operator station 220 includes several elements for interfacing with other elements of system 200. Specifically, operator station 220 includes imaging device interface 405, treatment head interface 310, gantry interface 315, and table interface 320.

Interfaces 305 through 320 may comprise dedicated hardware and/or software interfaces, and one or more of interfaces 305 through 320 may reside in processor 235. One or more of interfaces 305 through 320 may be implemented by a single interface. For example, interface 305 may be implemented by a single Ethernet interface and interfaces 310 through 320 may be implemented by a single proprietary interface for interfacing with table 255, treatment head 210, and gantry 215.

Processor 235 includes microprocessor 325 and memory 330. Microprocessor 325 may execute processor-executable program code stored in memory 330 to provide some or all of the functionality described herein. In this regard, memory 330 stores processor-executable process steps of dynamic strobe modulated ARC therapy manager 335.

Dynamic strobe modulated arc therapy manager 335 may comprise processor-executable program code to implement process steps described herein. Dynamic strobe modulated arc therapy manager 335 may also comprise program code to generate and/or modify a treatment plan according to some embodiments.

Memory 330 may also store treatment plans 340 in accordance with any currently- or hereafter-known format. Treatment plans 340 may comprise scripts that are automatically executable by linear accelerator 205 and treatment table 255 to provide radiation therapy fractions. Treatment plans 340 may include one or more treatment plans in which a patient position, a beam plan, and/or a prescribed dose that have been optimized according to some embodiments herein, including but not limited to a DAO algorithm.

Usage of each of modules 335 and 340 will be discussed below, and may comprise any suitable program code to perform the functions attributed thereto. Modules 335 and 340 may comprise any suitable software format, including but not limited to a dynamic link library, a plug-in, an operating system extension, a standalone application, etc. Dynamic strobe modulated arc therapy manager 335 may comprise module 340 or any other module such as a treatment planning module (not shown), according to some embodiments.

Figure 4:
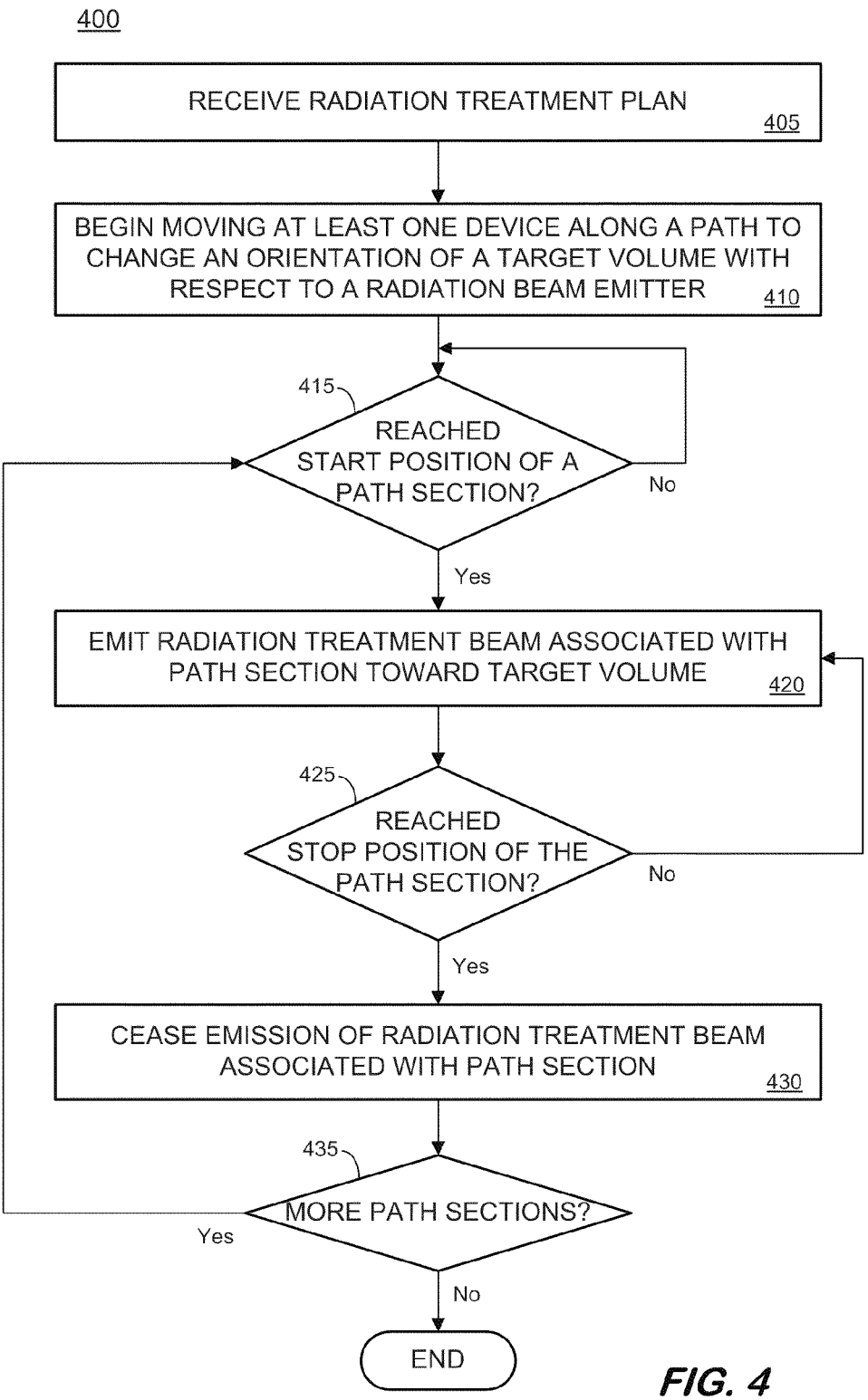
FIG. 4 comprises a flow diagram illustrating a dynamic strobe modulation ARC therapy processes, according to some embodiments.

FIG. 4 is an illustration of process 400, according to some embodiments. The illustrated process 400 may be implemented by any suitable hardware and/or software elements. Some embodiments may include hardware elements, some embodiments may include software elements, and other embodiments may include both software and hardware elements in the implementation of the illustrated processes, systems, and devices herein. The process of FIG. 4 is not limited to the order shown therein. Rather, embodiments of the process may be performed in any order that is practicable. For that matter, unless stated otherwise, any methods and processes disclosed herein may be performed in any order that is practicable. Notably, some embodiments may employ one or more portions of the process arranged in different configurations without one or more other portions of the process.

At 405, a radiation treatment plan for delivering at least a portion of a prescribed radiation dose to a target volume is received by a radiation therapy system. In some embodiments, the radiation treatment plan is provided to the radiation therapy treatment delivery system embodied in a computer or processor-readable medium such as a file or series of files embodied in a memory storage unit. The memory storage unit may be implemented as an optical disk, a CD-ROM, RAM, a flash ROM, or any type of memory storage unit now known or that becomes known in the future.

In some embodiments, the radiation treatment plan received or otherwise provided at 405 may be created using the Direct Aperture Optimization (DAO) algorithm. In accordance with the DAO algorithm, a series of individual radiation treatment beams are created and placed in a circular configuration around the patient. The location (e.g., angular position) of each beam is specified by a fixed point called the Optimization Point (OP). The shape and/or dose of each beam are optimized by the DAO algorithm to achieve a desired dose distribution within the patient based on the planning criteria.

The treatment plan may be created using planning algorithms other than the DAO algorithm. For example, the treatment planning algorithm, system or methodology used herein may include other treatment planning algorithms in addition to, or as a substitute for, the DAO algorithm.

A treatment planning system (not shown) may include a DAO planning system that generates, for example, thirty-six OP's spaced around the patient at 10 degree intervals. Again, each OP is associated with a radiation treatment beam, and the shape and the dose of each beam are optimized by the DAO algorithm to achieve an optimum dose distribution within the patient based on the planning criteria.

In some embodiments, a treatment delivery system executing process 400 converts each OP to a path section associated with a particular start position (e.g., angle) and a particular stop position (e.g., angle). Each path section represents a range over which a prescribed radiation dose associated with an OP is to be delivered, as opposed to being delivered at the fixed point specified by the OP. The received treatment plan may, of course, specify the path sections and their associated beams, which may be determined directly or from a DAO-generated treatment plan.

The path sections correspond to the path travelled by at least one device to change an orientation of a target volume with respect to the radiation beam emitter. As described above, the at least one device may comprise the radiation beam emitter itself, in which case the path sections include ranges of angles through which the gantry rotates. If the at least one device includes a treatment table, each OP may be converted to a path section corresponding to a continuous range of table positions.

Some embodiments may comprise movement of a radiation beam emitter and a treatment table (and/or other devices) during radiation beam emission. The movements of the devices generate a net change in the orientation of a target volume with respect to the radiation beam emitter during the radiation beam emission. In such embodiments, each OP may be converted to a path section for each of the devices in motion. For example, a single OP may be converted to a path section through which the radiation beam emitter is to be moved during delivery of a treatment radiation beam corresponding to the OP, and a path section through which the treatment table is to be moved during delivery of the treatment radiation beam corresponding to the OP.

The path section length may be determined such that the radiation dose distribution applied at a path section does not deviate more than a particular amount (e.g., 30%) from a radiation dose distribution achieved using an equivalent fixed-beam delivery mode. The lengths of the path sections may be limited to a particular maximum path section length.

A path section length may also be determined based on the time required by the at least one device to move along the path section and/or the dose rate with which radiation is to be applied. The system may optimize some or all of these parameters under the constraint that the time that is needed to apply the prescribed radiation is reduced or even minimized.

Assuming that the patient is positioned as required by the treatment plan, at least one device is moved along a path according to the treatment plan at 410. The movement changes an orientation of a target volume with respect to a radiation beam emitter. For purposes of the present example, it will be assumed that this movement consists of rotation of gantry 215 to rotate treatment head 210 in a circular arc around patient 240. In some embodiments, the gantry speed is adjusted to a pre-calculated value. The speed of the gantry may be calculated by using a prediction of a duration of movement along one or more path sections in order to minimize a treatment time while also satisfying the start position and stop position constraints of the path sections. The duration may include time for beam shaping, beam delivery, and other factors.

During the movement at 410, a beam shaping device(s) may be moved to a beam shape associated with an upcoming path section. The shape of the beam shaping device(s) may be verified and adjusted in a variety of different manners including, in some embodiments, in real-time as the gantry transitions from one path section to a next path section.

It will be assumed that treatment head 210 continues to move throughout the remainder of process 400, however, embodiments are not limited thereto. At 415, it is determined whether the at least one device (i.e., treatment head 210) has reached a start position of a path section. If not, flow pauses at 415 while the at least one device continues to move along the path. Once the start position is reached, a radiation beam associated with the path section is emitted toward the target volume at 420. In this regard, each path section may be associated with a plurality of beam parameters such as a beam shape, a beam energy and/or a radiation dose.

Emission of the radiation treatment beam at 420 may be accomplished in a number of different manners, including Precision Mode and Performance Mode. In Precision Mode, the dose rate of the beam is set such that, under constant gantry speed, the end of the dose delivery will coincide with the stop position. The dose is therefore delivered evenly over the entire path section.

In Performance Mode, the speed of the at least one device may be dynamically adjusted at or near the start position, at or near the stop position, and/or at or near a mid-point (or other multiple points) between the start position and the stop position. The speed of the at least one device, and other aspects of the delivery system, including but not limited to the size and energy of the treatment beam or the dose rate, may be dynamically adjusted based on different criteria related to the treatment plan and the target volume. In some embodiments, the rate of the beam distribution of the dose between the start position and the stop position may, either alone or in combination with other beam dose distribution optimization aspects, be maximized by using a beam without a flattening filter.

One or more beam parameters may remain constant during beam emission corresponding to a path section. Examples of these parameters include a beam shape, as may be defined by a collimator leaf arrangement and rotational setting, a beam energy, a speed of the beam emitter, a dose rate, and/or beam type (e.g. photon vs. electron). The use of one or more constant parameters simplifies system control. Of course, one or more of the above or other beam parameters may change during beam emission along a path section.

The emission continues until it is determined that a stop position of the path section is reached at 425. Accordingly, at 430, emission of the radiation beam associated with the path section ceases. At 435 it is determined whether the path includes more path sections. If so, flow returns to 415.

As noted above, a stop position of a path section may be spaced apart from a start position of a next path section. Accordingly, flow may again cycle at 415 until the at least one device reaches the start position of a next path section. During this time, the radiation delivery system may prepare to emit a radiation beam associated with the next path section. For example, a MLC shape may be changed during this time from a beam shape associated with the previously-emitted beam to a beam shape associated with the beam that is next to be emitted.

Process 400 terminates once it is determined at 435 that no further path sections exist in the present treatment plan.

Some embodiments may provide several advantages over systems in which a gantry moves continuously and applies radiation continuously. Due to the ability to change system settings during gaps between the path sections, therapy planning is subject to fewer system constraints. Since no radiation is applied within the gaps, the system may change parameter settings with a high degree of freedom, including parameter settings which are non-contiguous or which cannot be changed while radiation is being emitted.

Some embodiments also permit higher dose rates than the above conventional systems, which must reduce the dose rate because the beam is continuously on.

Some embodiments may be referred to as a "burst-mode" scheme or a "strobe-mode" scheme because radiation is emitted only at defined path sections. During such bursts, the dose rate may be much higher (e.g., more than 1000 MU/min, 2000 MU/min, 3000 MU/min or 4000 MU/min) than that used in conventional continuous application schemes. Consequently, radiation is emitted over a shorter total time.

The overall time during which radiation is applied may be less than 60% of the time required for the at least one device to travel along the entire path. Also or alternatively, the length of all the path sections along which radiation is applied may total less than 60% of the entire path length.

Figure 5:
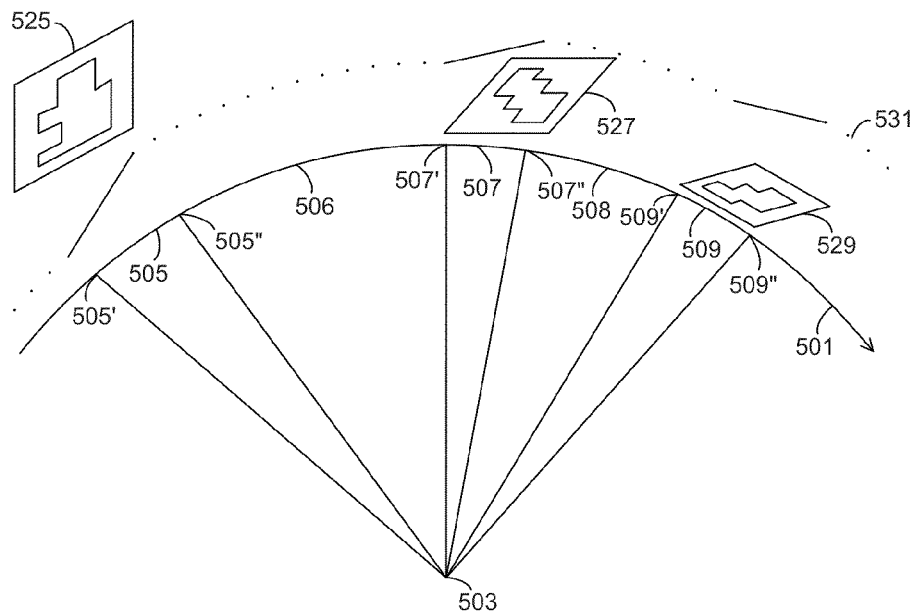
FIG. 5 shows path sections of a portion of a path along which a radiation emitter of a radiation therapy system moves, according to some embodiments.

FIG. 5 provides illustrates execution of process 400 according to some embodiments in which a gantry is moved to change the orientation of a target volume with respect to the treatment head. As shown, a gantry moves along a circular arc 501 around an isocenter 503. A target volume (not shown) is positioned at isocenter 503.

Three path sections 505, 507, 509 are distributed along arc 501. Each path section 505, 507, 509 is characterized by a start angle 505', 507', 509' and by a stop angle 505'', 507'', 509''. A treatment radiation beam corresponding to path section 505 is emitted when a gantry reaches start angle 505'. The beam is emitted while the gantry moves along the first path section 505, and emission ceases when the gantry reaches stop angle 505''. During this beam emission, beam parameters as beam energy, dose rate and beam shape 525 are assumed to remain constant, although embodiments are not limited thereto.

Any of the beam energy, the dose rate and/or the beam shape 525 may be set to a new value as the gantry moves along the gap 506 between path section 505 and path section 507. In the present example, beam shape 525 is changed to beam shape 527. The gantry speed may also be adjusted, for example, if additional time for setting the new values is required. However, the gantry can move as fast as possible to the next start angle 507' to reduce overall process time. If desired, a verification step to verify the correct setting changes may be carried out before the gantry reaches start angle 507' of second path section 507.

A treatment radiation beam corresponding to path section 507 is emitted when a gantry reaches start angle 507'. The beam is emitted while the gantry moves along the first path section 507, and emission ceases when the gantry reaches stop angle 507''.

The process repeats for gap 508 and path section 509 and until the last path section has been traversed.

In the foregoing example, the dose applied to the target volume (dose curve 531) continuously increases at the path sections 505, 507, 509.

Figure 6:
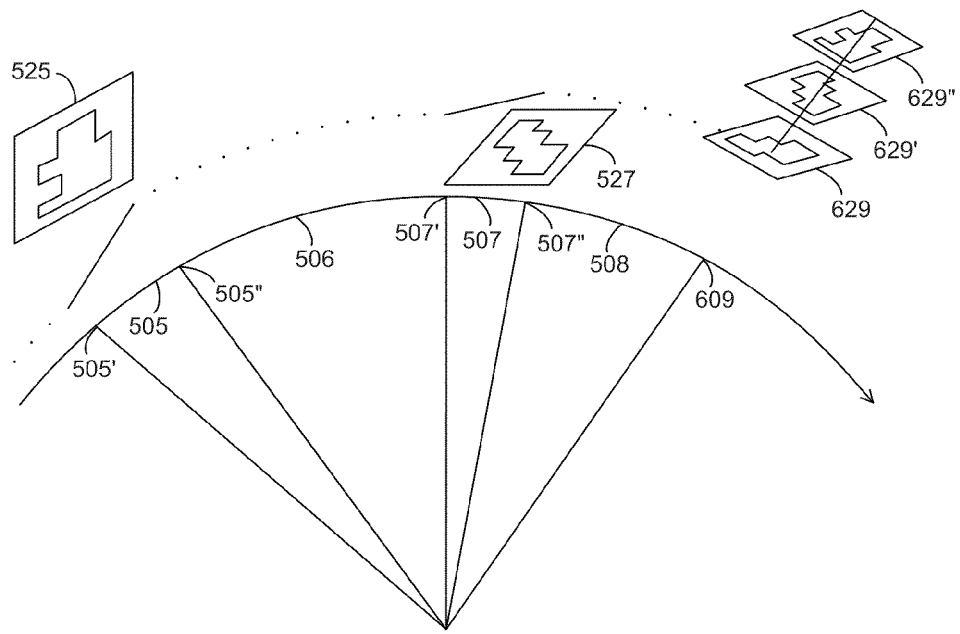
FIG. 6 shows path sections of a portion of a path along which a radiation emitter of a radiation therapy system moves, according to some embodiments.

FIG. 6 illustrates a different embodiment of process 600. The first and the second path sections 505, 507 correspond to the first and the second path sections of FIG. 5. The third path section 609, however, is associated with a start position that coincides with its stop position. The beam parameters are set to the values associated with third path section 609 in gap 508 between path section 507 and path section 609.

Gantry movement stops as soon as the gantry reaches path section 609. After stopping, a first radiation beam associated with path section 609 is emitted. Next, beam parameters are changed (for example, changing beam shape 629 to beam shape 629') and a next radiation beam associated with path section 609 is emitted. In some embodiments, beam parameters may change during the emission of radiation. For example, settings of a beam shaping device may change as radiation passes through the beam shaping device. A third radiation beam associated with path section 609 (and having beam shape 629'') is then emitted and the gantry resumes its rotation until the next path section is reached.

Figure 7:
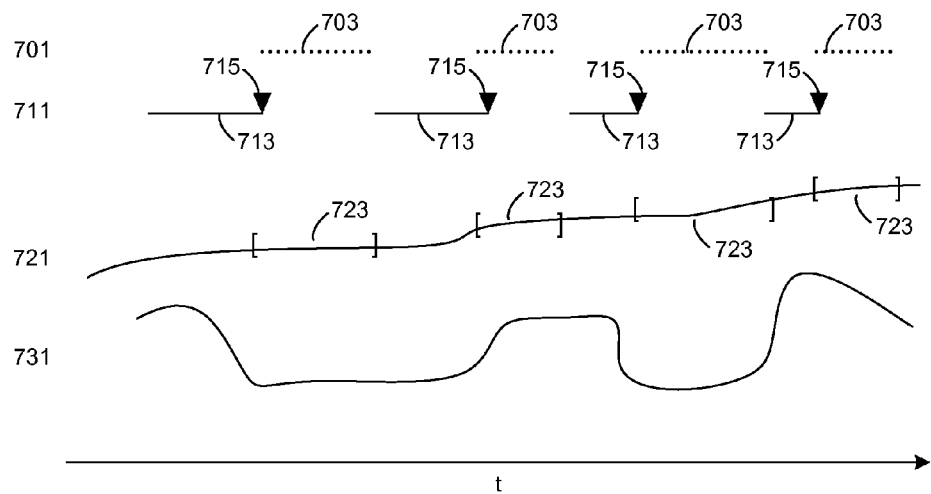
FIG. 7 illustrates emission of radiation over time, according to some embodiments.

FIG. 7 illustrates a dynamic process of radiation application according to some embodiments.

Upper part 701 shows periods (dotted line segments 703) during which radiation is emitted. A value of a discrete parameter 711 (e.g., the collimator setting) is also represented. Specifically, plain line segments 713 indicate time periods during which the discrete parameter is changed. These periods are arranged in the gaps between radiation emission. Verification step 715 is executed to verify the correct setting at the end of time periods 713. The behavior of the discrete parameter during time periods 713 may be completely non-linear.

Shown below the time course of discrete parameter 711 is continuous parameter 721 (i.e., a parameter that changes during the periods of radiation emission and during the gaps between those periods). Brackets 723 indicate predefined radiation application windows. Such windows correspond to predefined path sections that impose a constraint on actual path sections along which radiation is applied. Actual path sections must fit within predefined path sections in the illustrated embodiment. The system may not allow emission of radiation outside those windows.

Continuous parameter 731 is also shown. Continuous parameter 931 may relate to the speed of the gantry.

Figure 8:
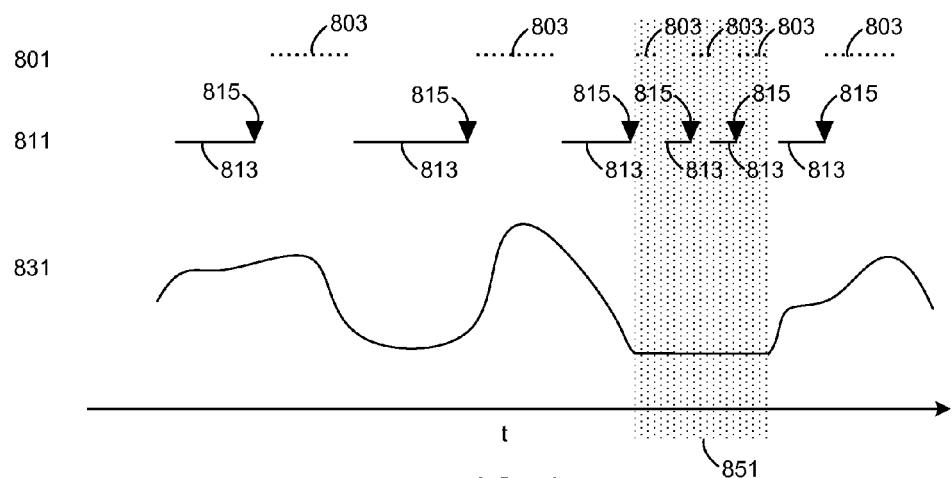
FIG. 8 illustrates emission of radiation over time, according to some embodiments.

FIG. 8 illustrates a dynamic process of radiation application according to the some embodiments.

Static phase 851 interrupts movement of the gantry. The speed-modulated parameter 831 stops to vary during the static phase 851, at which radiation may be turned on and off several times. Parameter settings 813 of discrete parameters 811 may be changed during these bursts of static phase 851. After static phase 851, the gantry may resume movement and radiation may be emitted as described herein.

Some embodiments may be configured, adapted, or otherwise have functionality to handle exceptions or special situations that may occur in conjunction with process 400. For example, if the time period between path sections is not sufficient to configure a beam shaping device for a next treatment beam, the movement of the at least one device may decelerate such that the next treatment beam can be delivered within the prescribed start position and stop position for the next path section. If the beam shaping device fails for some reason to configure into the desired shape (or if any other parameter of the next path section's radiation beam cannot be set), the treatment may be interrupted (i.e., aborted).

It is noted that process 400 may encompass other modes of radiation therapy. For example, conventional IMRT may be expressed as a special case of process 400 wherein the start position and stop position of any given path section are equal to each other. Accordingly, each prescribed radiation beam will be delivered with a stopped gantry, rather than being delivered with a moving gantry.

In some embodiments, hybrid delivery plans may be developed and executed that may include at least one 'standard' IMRT portion, as well as at least one 'dynamic strobe' portion, to meet the treatment objectives. In this manner, a hybrid delivery plan may be developed and administered that includes the advantages of both methods (faster delivery with higher precision where required). For example, a hybrid treatment scheme may provide the accuracy of fixed IMRT in the most critical areas, while preserving the speed advantage of the 'dynamic strobe' delivery wherever accuracy has less impact on the estimated dosimetric calculation.

In some embodiments, path sections of a treatment plan may be arranged to accomplish treatment delivery in a least amount of time. This arrangement may consider a single pass of 360 (or less) degrees of rotation, or multiple passes, as needed. In the instance of a single-pass mode, overlapping path sections may be re-ordered and re-sized so that each path section can be delivered within the path section's own start position and stop position. The path sections may then be re-sorted so that they can be delivered along the expected path.

It is noted that sequence of path sections described by a treatment planning system, sub-system, mechanism, or module need not be the same as the sequence of path sections re-organized by the intelligence of the delivery system.

In some embodiments, the systems and methods herein may support clockwise and counterclockwise delivery, and the direction may be changed dynamically based upon the position of the at least one device when the patient is positioned in the delivery system. For each path section, the gantry speed may be calculated such that all the parameters of the treatment plan can be achieved, taking into account the limitations of the system.

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. A method executed by an apparatus in response to execution of program code by a processor of the apparatus:
   moving at least one device along a path to change an orientation of a target volume with respect to a radiation beam emitter;
   determining that the at least one device has reached a start position of a first path section associated with a first radiation treatment beam;
   while moving the at least one device along the first path section, emitting the first radiation treatment beam from the radiation beam emitter toward the target volume;
   determining that the at least one device has reached a stop position of the first path section;
   ceasing emission of the first radiation treatment beam in response to the determination that the at least one device has reached the stop position of the first path section;
   determining that the at least one device has reached a start position of a second path section associated with a second radiation treatment beam, the start position of the second path section being different from the stop position of the first path section; and
   while moving the at least one device along the second path section, emitting the second radiation treatment beam from the radiation beam emitter toward the target volume.

2. The method of claim 1, wherein a beam shape and/or a beam energy is kept constant during beam emission between the start position and the stop position of least one of the first and second path sections.

3. The method of claim 1, wherein at least one of the first and second path sections is associated with a start position equal to its stop position.

4. The method of claim 3, wherein a plurality of successive beam shapes are applied at the path section having the start position equal to its stop position.

5. The method of claim 1, further comprising determining the first radiation treatment beam and the first path section based on a fixed radiation treatment beam associated with a fixed point along the first path section.

6. The method of claim 1, wherein the length of the first path section and the length of the second path section are less than a predefined path section length.

7. The method of claim 1, wherein the first radiation treatment beam distributes a radiation dose substantially equally between the start position and the stop position of the first path section.

8. The method of claim 1, wherein the path comprises a plurality of other path sections, the method further comprising:
   while moving the at least one device along each of the plurality of other path sections, emitting a radiation treatment beam respectively corresponding to each path section toward the target volume,
   wherein, in sum, each radiation treatment beam emitted while moving along the path delivers a prescribed radiation dose toward the target volume.

9. A method according to claim 1, wherein the at least one device comprises the radiation beam emitter.

10. A method according to claim 1, wherein the at least one device comprises a table, wherein the target volume is disposed within a patient, and wherein the patient is disposed on the table.

11. A method according to claim 10, wherein the at least one device comprises the radiation beam emitter.

12. A system comprising:
   a radiotherapy device comprising a radiation beam emitter;
   a memory to store a radiation treatment plan; and
   a control unit in communication with the memory and operable to execute the radiation treatment plan to:
      moving at least one device along a path to change an orientation of a target volume with respect to radiation beam emitter;
      determine that the at least one device has reached a start position of a first path section associated with a first radiation treatment beam;
      while the at least one device moves along the first path section, emit the first radiation treatment beam from the radiation beam emitter toward a target volume;
      determine that the at least one device has reached a stop position of the first path section;
      cease emission of the first radiation treatment from the radiation beam emitter in response to the determination that the at least one device has reached the stop position of the first path section;
      determine that the at least one device has reached a start position of a second path section associated with a second radiation treatment beam, the start position of the second path section being different from the stop position of the first path section; and
      while the at least one device moves along the second path section, emit the second radiation treatment beam from the radiation beam emitter toward the target volume.

13. The system of claim 12, wherein a beam shape and/or a beam energy is kept constant during beam emission between the start position and the stop position of least one of the first and second path sections.

14. The system of claim 12, wherein at least one of the first and second path sections is associated with a start position equal to its stop position.

15. The system of claim 14, wherein a plurality of successive beam shapes are applied at the path section having the start position equal to its stop position.

16. The system of claim 12, the control unit further operable to execute the radiation treatment plan to determine the first radiation treatment beam and the first path section based on a fixed radiation treatment beam associated with a fixed point along the first path section.

17. The system of claim 12, wherein the length of the first path section and the length of the second path section are less than a predefined path section length.

18. The system of claim 12, wherein the first radiation treatment beam distributes a radiation dose substantially equally between the start position and the stop position of the first path section.

19. The system of claim 12, wherein the path comprises a plurality of other path sections, the control unit further operable to execute the radiation treatment plan to:
while the at least one device moves along each of the plurality of other path sections, emit a radiation treatment beam respectively corresponding to each path section from the radiation beam emitter toward the target volume,
wherein, in sum, each radiation treatment beam emitted while moving along the path delivers a prescribed radiation dose toward the target volume.

20. A system according to claim 12, wherein the at least one device comprises the radiation beam emitter.

21. A system according to claim 12, wherein the at least one device comprises a table, wherein the target volume is disposed within a patient, and wherein the patient is disposed on the table.

22. A system according to claim 21, wherein the at least one device comprises the radiation beam emitter.

23. A non-transitory computer-readable medium storing program code executable by a processor to:
move at least one device along a path to change an orientation of a target volume with respect to a radiation beam emitter;
determine that the at least one device has reached a start position of a first path section associated with a first radiation treatment beam;
while the at least one device moves along the first path section, emit the first radiation treatment beam from the radiation beam emitter toward a target volume;
determine that the at least one device has reached a stop position of the first path section;
cease emission of the first radiation treatment from the at least one device in response to the determination that the at least one device has reached a stop position of the first path section;
determine that the at least one device has reached a start position of a second path section associated with a second radiation treatment beam, the start position of the second path section being different from the stop position of the first path section; and
while the at least one device moves along the second path section, emit the second radiation treatment beam from the radiation beam emitter toward the target volume.

24. The medium of claim 23, wherein a beam shape and/or a beam energy is kept constant during beam emission between the start position and the stop position of least one of the first and second path sections.

25. The medium of claim 23, wherein at least one of the first and second path sections is associated with a start position equal to its stop position.

26. The medium of claim 23, wherein the first radiation treatment beam distributes a radiation dose substantially equally between the start position and the stop position of the first path section.

27. The medium of claim 23, wherein the at least one device comprises the radiation beam emitter.

28. The medium of claim 23, wherein the at least one device comprises a table, wherein the target volume is disposed within a patient, and wherein the patient is disposed on the table.

29. The medium of claim 28, wherein the at least one device comprises the radiation beam emitter.

* * * * *